(12) United States Patent
Masson

(10) Patent No.: US 8,968,322 B1
(45) Date of Patent: Mar. 3, 2015

(54) METHOD AND COMPOSITION FOR REPAIR OF ARTICULAR BONE FRACTURES

(71) Applicant: Marcos V. Masson, Houston, TX (US)

(72) Inventor: Marcos V. Masson, Houston, TX (US)

(*) Notice: Subject to any disclaimer, the term of this patent is extended or adjusted under 35 U.S.C. 154(b) by 236 days.

(21) Appl. No.: 13/650,406

(22) Filed: Oct. 12, 2012

Related U.S. Application Data

(63) Continuation-in-part of application No. 12/510,838, filed on Jul. 28, 2009, now abandoned.

(60) Provisional application No. 61/090,218, filed on Aug. 19, 2008.

(51) Int. Cl.
*A61B 17/58* (2006.01)
*A61B 17/60* (2006.01)
*A61F 2/00* (2006.01)
*A61M 29/00* (2006.01)
*A61B 17/88* (2006.01)

(52) U.S. Cl.
CPC .................................. *A61B 17/8811* (2013.01)
USPC .............................................. 606/92; 606/192

(58) Field of Classification Search
USPC ..................................... 606/86 R, 92–94, 192
See application file for complete search history.

(56) References Cited

U.S. PATENT DOCUMENTS 8,403,937 B2 * 3/2013 Schwardt et al. ............... 606/92
2002/0099385 A1 * 7/2002 Ralph et al. ..................... 606/92

* cited by examiner

*Primary Examiner* — Andrew Yang
*Assistant Examiner* — Diana S Jones
(74) *Attorney, Agent, or Firm* — Egbert Law Offices, PLLC

(57) ABSTRACT

A method of repairing a fractured articular bone at a fracture site has the steps of mixing a bone glue, inserting an expandable balloon into the fracture site, inflating the expandable balloon at the fracture site, applying the bone glue to the fracture site while the expandable balloon is inflated, curing the bone glue at the fracture site while the expandable balloon is inflated, deflating the expandable balloon after the bone glue has cured, and removing the deflated expandable balloon from the fracture site and from the articular bone. The bone glue combines a biologically dissolvable glue with an actual or artificial particulate bone graft.

13 Claims, 3 Drawing Sheets

METHOD AND COMPOSITION FOR REPAIR OF ARTICULAR BONE FRACTURES

CROSS-REFERENCE TO RELATED U.S. APPLICATIONS

The present application is a continuation-in-part of U.S. patent application Ser. No. 12/510,838, filed on Jul. 28, 2009, and entitled "METHOD AND COMPOSITION FOR REPAIR OF ARTICULAR BONE FRACTURES", presently pending. U.S. application Ser. No. 12/510,838 claims priority from U.S. Provisional Patent Application Ser. No. 61/090,218, filed on Aug. 19, 2008, and entitled "METHOD AND COMPOSITION FOR REPAIR OF ARTICULAR BONE FRACTURES".

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention is related to the repair of fractured bones. More particularly, the present invention is related to articular bones. More particularly, the present invention the related to mixtures of glue used to repair a fractured articular bone.

2. Description of Related Art Including Information Disclosed Under 37 CFR 1.97 and 37 CFR 1.98

Bone fractures occur when a bone is cracked or broken. Fractures often occur when a bone is subject to a great force of impact or stress. Fractures can occur in any bone of the human body, including the articular, or joint, bones.

When repairing a bone fracture, it is common to first realign the bone at the fracture site. Various techniques are used to realign the bone. For example, metal rods or plates can be used to keep the bones in alignment. The metal rods and plates are usually affixed to the bone with screws. Another technique involves aligning the two parts of the fractured bone with an expandable balloon. The fractured parts of the bone are aligned with the expandable balloon, and devices, such as clamps, are compressed around the fracture so as to close the fracture site. Sometimes bone cement is used when using an expandable balloon and clamps so as to fill voids in the fracture site and add strength to the bone. Bone cement is typically used to hold implants in a fractured bone. The bone cement sets-up so as to hold implants in the bone.

However, the cement is inadequate for repairing articular bone fractures because it is not an adhesive. Bone cement is somewhat of a misnomer. The word "cement" typically describes a substance that adheres things together. Bone cement, however, is actually a grout-like material. Bone cement acts as a space-filler so as to fill the voids in the bone where implants are placed. Thus, bone cement is highly inadequate for repairing a fracture in an articular bone. Thus, there is a need for a method for repairing articular bone that utilizes a bone glue that is adequate for repairing the fracture.

Various patents have issued relating to the repair of fractured bones. For example, U.S. Pat. No. 5,648,310, issued on Aug. 19, 1997 to Berger, discloses a method and apparatus for forming an internal fixation of fractures of tubular bones using a balloon catheter fixation device which is guided and transported through the medullary canal and fracture site of the bone by guide wires mounted in the balloon catheter fixation device. A bone cement is applied to the fracture site. The bone catheter is inflated inside the bone and tightened by applying pressure on the catheter outside of the bone. The catheter tube is tightened and held in the same place in an inflated condition so as to apply a compression force across the fracture site enhancing the stability of the fractured bone and promoting osseous healing.

U.S. Patent Publication No. 2005/0010297, published on Jan. 13, 2005 to Watson et al., discloses a medical device containing an inflatable balloon structure for use in minimally invasive surgery and minimally invasive diagnostic and therapeutic procedures. The device is delivered by a catheter and expanded by using gases, liquids or liquids that solidify in situ. The inflatable balloon may be constructed from a wide variety of materials and may be reinforced by supporting structures. The device may form an endoprosthesis in a patient. The device may be used in combination with bone graft materials.

U.S. Pat. No. 4,313,434, issued on Feb. 2, 1982 to Segal, discloses a method for fixation of a long bone including the steps of drilling a small opening into the medullary cavity, inserting a deflated flexible bladder into the medullary cavity through the opening, inflating the bladder with sterile air through an opening accessible outside the bone, sealing the opening, unsealing the opening after the fracture has healed, removing the bladder and then filling the opening.

U.S. Pat. No. 6,280,456, issued on Aug. 28, 2001 to Scribner, et al., discloses a method for treating a bone that employs a tool having an outer catheter tube having a distal end and an inner catheter tube extending within the outer catheter tube that has a distal end region that extends beyond the distal end of the outer catheter tube. The tool includes an expandable structure having a proximal end secured to the distal end of the outer catheter tube and a distal end secured to the distal end region of the inner catheter tube. Thus, the distal end region of the inner catheter tube is enclosed within the expandable structure. The method manipulates the tool to introduce the expandable structure into a bone while in a generally collapsed geometry. The method causes the expandable structure to assume an expanded geometry inside the bone.

U.S. Pat. No. 6,140,452, issued Oct. 31, 2000 to Felt et al. discloses a method, composition, and apparatus for repairing a tissue site. The method involves the use of a curable polyurethane biomaterial composition adapted for mixing at the time of use in order to provide a flowable composition and to initiate cure. The flowable composition can be delivered in a minimally invasive manner to a tissue site. The composition fully cures to provide a permanent and biocompatible prothesesis for repair of the tissue site. A mold apparatus has a balloon or tubular cavity that receives a biomaterial composition. The method includes the steps of delivering and filling the mold apparatus with a curable composition in situ to provide a prostheses for tissue repair.

It is an object of the present invention to provide a method for repairing articular bones.

It is another object of the present invention to provide a method for repairing articular bones that adheres the fractured portions together.

It is another object of the present invention to provide an articular bone repair method that properly aligns the fractured portions of the bone.

It is another object of the present invention to provide a method for repairing fractured articular bones that minimizes the number of steps in the procedure.

It is still another object of the present invention to provide a method for repairing articular bones that minimizes the healing time of the fractured bone.

It is another object of the present invention to provide a method for repairing articular bones that can be applied to any joint of the human body.

These and other objects and advantages of the present invention will become apparent from a reading of the attached specification and appended claims.

BRIEF SUMMARY OF THE INVENTION

The present invention is a method of repairing a fractured articular bone at a fracture site. The method includes the steps of: (1) mixing a bone glue; (2) inserting an expandable balloon into the fracture site; (3) inflating the expandable balloon at the fracture site; (4) applying the bone glue to the fracture site while the expandable balloon is inflated; (5) curing the bone glue at the fracture site while the expandable balloon is inflated; (6) deflating the expandable balloon after the bone glue has cured; and (7) removing the deflated expandable balloon from the fracture site and from the articular bone.

The expandable balloon is deflated prior to the step of removing the expandable balloon. The step of inserting includes inserting an expandable balloon into an interior of a first piece of the fractured bone and into an interior of a second piece of the fractured bone so as to align the first piece and the second piece during the step of inflating the expandable balloon. The step of applying includes applying the bone glue to the fracture site in a gap that is present between the first piece of the fractured bone and the second piece of the fractured bone.

The bone glue can have adhesive properties. This bone glue can include a particulate bone graft and a biologically dissolvable glue. The bone graft is can either be an artificial bone graft or an actual human bone graft.

This foregoing section is intended to describe, with particularity, the preferred embodiment of the present invention. It is understood that modifications to this preferred embodiment can be made in accordance with the present invention. As such, this section should not to be construed, in any way, as limiting of the broad scope of the present invention. The present invention should only be limited by the following claims and their legal equivalents.

DETAILED DESCRIPTION OF THE INVENTION

Figure 1:
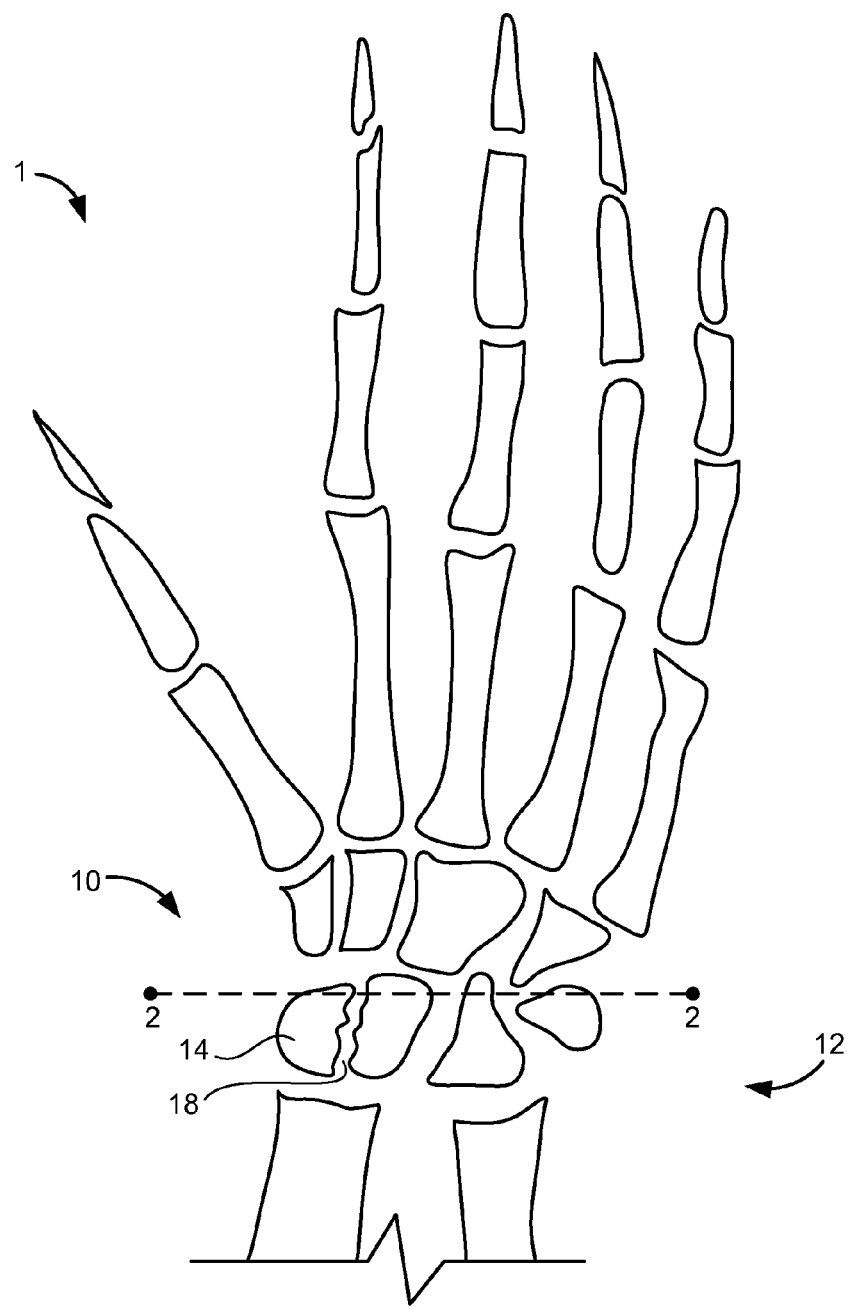
FIG. 1 shows a top view of the bones of a human hand.

Referring to FIG. 1, there is shown a top view of the bones of human hand 1. The bones of the human hand 1 include the articular bones 10 of the wrist 12. A fracture 16 can be seen in carpal 14 of the wrist 12. Thus, there is a fracture 16 in one of the articular bones 10 of the hand 1.

Figure 2:
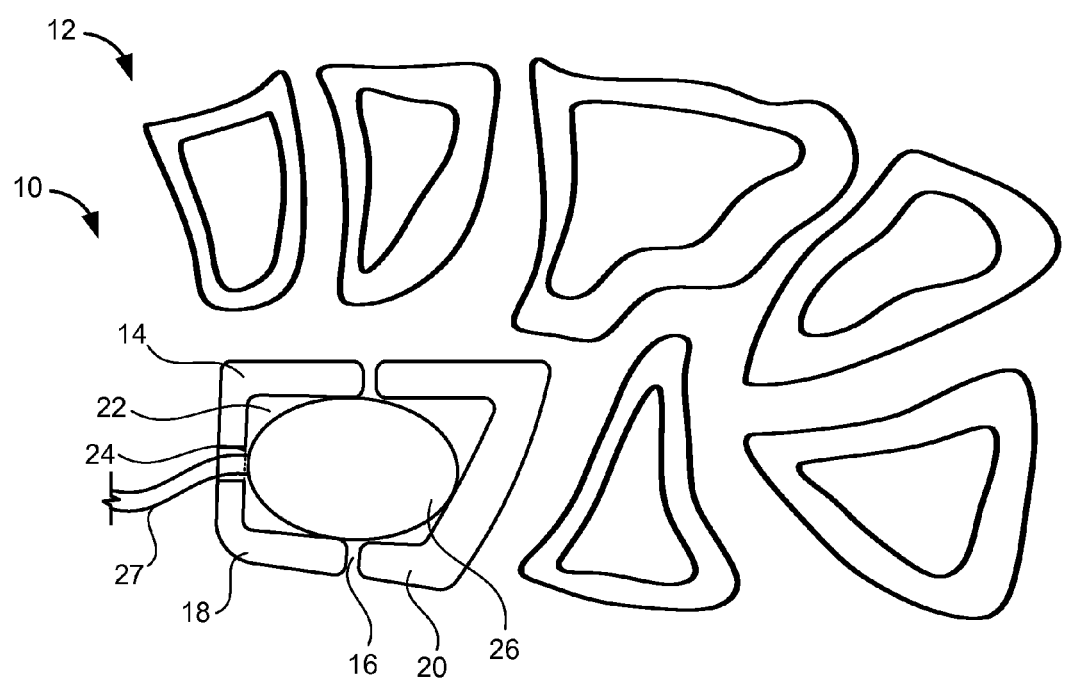
FIG. 2 shows an isolated cross-sectional perspective view of a the articular bone bones of the wrist, with the fracture carpal having an expandable balloon inserted therein, taken along sight line 2-2 of FIG. 1.

Referring to FIG. 2, there is shown an isolated cross-sectional view of a the articular bones 10 of the wrist 12 taken along sight line 2-2 in FIG. 1. The fractured carpal 14 has a first piece 18 and a second piece 20. An expandable balloon 26 is inserted in the interiors 22 of the first piece 18 and second piece 20 so as to align the first piece 18 and the second piece 20. As is often the case with bone fractures, the first piece 18 and the second piece 20 of the carpal 14 do not fit perfectly back together. Thus, there is a slight gap between the two pieces 18 and 20 of the carpal 14.

The expandable balloon 26 was in a deflated configuration prior to insertion into the interior 22 of the carpal 14. The deflated balloon 26 was inserted through hole 24 of the carpal 14. The hole 24 was formed by conventional bone repair methods. Once in the interior 22 of the carpal 14, the balloon 26 was expanded so as to align the first piece 18 and the second piece 20. FIG. 2 shows that the balloon 26 has a tube 27 connected thereto. The tube 27 allows the balloon to be inflated with a gas or a liquid from outside of the fracture site.

Figure 3:
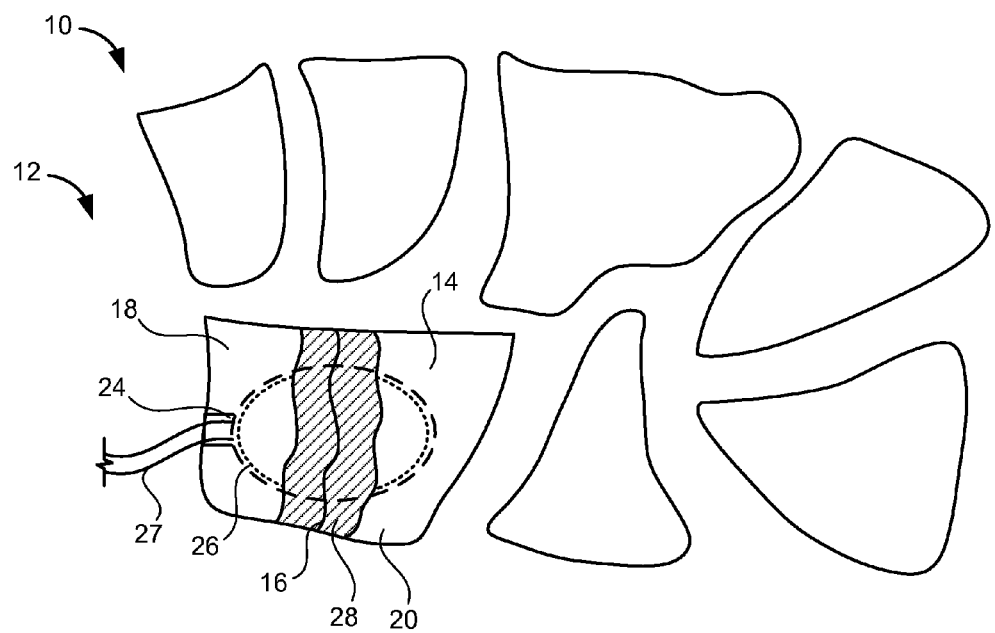
FIG. 3 shows an isolated top view of the articular bones of the wrist, with bone glue applied to the fracture according to the method of the present invention.

Referring to FIG. 3, there is shown a top view of the articular bones 10 of the wrist 12. A bone glue 28 was mixed and applied to the fracture 16 of the carpal 14 while the expandable balloon 26 is inflated. The bone glue 28 is biologically dissolvable. The bone glue 28 is made by mixing a bone graft with a biologically dissolvable glue. The bone graft can be an actual bone graft or an artificial bone graft. When applied to the fracture 16, the bone glue 28 holds the shape of the carpal 14 and holds the first piece 18 with the second piece 20 for a length of time sufficient for the intrinsic healing of the body to begin. The bone glue 28 is different from bone cement in that a bone cement merely holds bones in place, while the bone glue 28 of the present invention adheres the first piece 18 with the second piece 20 so as to hold the two pieces 18 and 20 together at the fracture 16 so that the carpal 14 can heal.

The bone glue 28 is cured while the expandable balloon is inflated so that the structure of the first piece 18 and the second piece 20 of the carpal 14 is maintain in a proper configuration. Once the bone glue 28 has cured, the expandable balloon 26 is deflated. The deflated balloon 26 can then be withdrawn from the carpal 14 through the hole 24.

Figure 4:
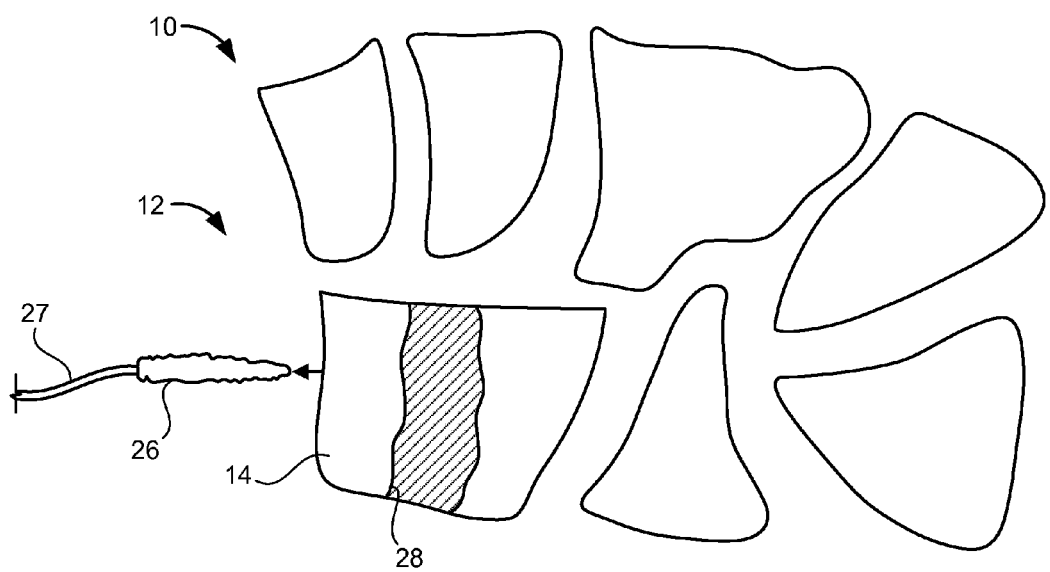
FIG. 4 shows an isolated top view of the articular bones of the wrist, with the fractured carpal healed according to the method of the present invention.

Referring to FIG. 4, there is shown a top view of the articular bones 10 of the wrist 12, with the fracture healed. The bone glue 28 can be seen on the carpal 14 of the wrist 12. The fracture is no longer visible because it has healed. The bone glue 28 is biologically dissolvable. Therefore, the bone glue 28 will disappear over time as it dissolves into the body of the patient. FIG. 4 shows that the balloon 26 and the tube 27 are removed through the hole 24 when the balloon 26 is deflated and after the bone glue 28 has cured.

The expandable balloon 26 is utilize to provide the structure for the repair of the fracture site during the entire process of using the balloon. As such, the method the present invention avoids the use of multiple pins. The present invention utilizes the balloon to provide the primary structure during the period that the bone glue 28 cures. As such, it is less invasive than prior art processes.

In the field of the repair of articular bone fractures, pins have been used in the prior art so as to maintain the structure of the fracture site. Such pins can actually restrict movement and, as such, would not be suitable for the repair of an articular bone. The expandable balloon 26 of the present invention can ultimately allow for more freedom of motion in the area of the joint site.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

I claim:

1. A method of repairing a fractured articular bone at a fracture site, the method comprising:
    mixing a bone glue;
    inserting an expandable balloon into the fracture site;
    inflating the expandable balloon at the fracture site;
    applying said bone glue to the fracture site while said expandable balloon is inflated;
    curing the bone glue at the fracture site while said expandable balloon is inflated;
    deflating said expandable balloon after said bone glue has cured; and
    removing the deflated expandable balloon from the fracture site and from the articular bone.

2. The method of claim 1 further comprising the step of:
    deflating said expandable balloon prior to said step of removing said expandable balloon.

3. The method of claim 1, said step of inserting comprising:
    inserting an expandable balloon through an interior of a first piece of the fractured bone and an interior of a second piece of the fractured bone so as to align the first piece and the second piece during said step of inflating the expandable balloon.

4. The method of claim 1, said step of applying comprising:
    applying the bone glue to the fracture site in a gap that is present between the first piece of the fractured bone and the second piece of the fractured bone.

5. The method of claim 1, said bone glue having adhesive properties.

6. The method of claim 1, said bone glue comprising:
    a particulate bone graft; and
    a biologically dissolvable glue.

7. The method of claim 6, said bone graft being an artificial bone graft.

8. A method for repairing an articular bone fracture at a fracture site, the method comprising:
    mixing an adhesive bone glue, said adhesive bone glue comprising:
        a bone graft; and
        a biologically dissolvable glue;
    inserting an expandable balloon into the fracture site;
    inflating said expandable balloon at the fracture site of the articular bone;
    applying said bone glue to the fracture site while said expandable balloon is inflated;
    curing said bone glue at the fracture site while said expandable balloon is inflated; and
    removing said expandable balloon from the articular bone after said bone glue has cured.

9. The method of claim 8, further comprising the step of:
    forming an opening in the articular bone, said step of forming occurring prior to said step of inserting, said expandable balloon being inserted through said opening.

10. The method of claim 8, further comprising the step of:
    deflating said balloon prior to said step of removing said expandable balloon.

11. The method of claim 8, said step of inserting comprising:
    inserting an expandable balloon through interiors of a first piece of the fractured bone and a second piece of the fractured bone so as to align the first piece and the second piece during said step of inflating the expandable balloon.

12. The method of claim 11, said step of applying comprising:
    applying said bone glue to the fracture site in a gap that is present between the first piece of the fractured bone and the second piece of the fractured bone.

13. The method of claim 8, said bone graft being an artificial bone graft.

* * * * *